United States Patent [19]

Felix

[11] Patent Number: 4,525,311

[45] Date of Patent: Jun. 25, 1985

[54] O,O-DIALKYL-N-(BENZYL OR T-BUTYL)-N-CYANOMETHYL AMINOMETHYLPHOSPHONATES

[75] Inventor: Raymond A. Felix, Richmond, Calif.

[73] Assignee: Stauffer Chemical Company, Westport, Conn.

[21] Appl. No.: 553,452

[22] Filed: Nov. 21, 1983

Related U.S. Application Data

[62] Division of Ser. No. 391,023, Jun. 22, 1982.

[51] Int. Cl.$^3$ ................................................. C07F 9/40
[52] U.S. Cl. .............................. 260/940; 260/502.5 F
[58] Field of Search ......................................... 260/940

[56] References Cited

U.S. PATENT DOCUMENTS 4,235,809 11/1980 Redmore ..................... 260/502.5 E Primary Examiner—Anton H. Sutto
Attorney, Agent, or Firm—Edwin H. Baker

[57] ABSTRACT

A method of preparing N-phosphonomethylglycine comprising reacting a compound having the structural formula

R—NHCH$_2$CN wherein R is tertiary butyl or

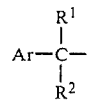

wherein Ar is an aromatic group, R$^1$ and R$^2$ are independently hydrogen, C$_1$–C$_{10}$ alkyl or an aromatic group, with formaldehyde and a phosphite to form a tertiary amine and hydrolyzing the tertiary amine in the presence of hydrochloric, hydrobromic, or hydriodic acid to yield N-phosphonomethylglycine.

3 Claims, No Drawings

4,525,311

O,O-DIALKYL-N-(BENZYL OR T-BUTYL)-N-CYANOMETHYL AMINOMETHYLPHOSPHONATES

This is a divisional of application Ser. No. 391,023, filed June 22, 1982.

FIELD OF THE INVENTION

This invention is a new process for preparing N-phosphonomethylglycine.

BACKGROUND OF THE INVENTION

N-Phosphonomethylglycine and certain salts are particularly effective as a post-emergence herbicide. The commercial herbicide is sold as a formulation containing the isopropylamine salt of N-phosphonomethylglycine.

N-Phosphonomethylglycine can be made by a number of methods. One such method, as described in U.S. Pat. No. 3,160,632 is to react N-phosphinomethylglycine (glycinemethylenephosphonic acid) with mercuric chloride in a water solvent at reflux temperature, and subsequently separating the reaction products. Other methods are phosphonomethylation of glycine and the reaction of ethyl glycinate with formaldehyde and diethylphosphite. The latter method is described in U.S. Pat. No. 3,799,758. In addition, there is a series of patents relating to the preparation of N-phosphonomethylglycine, including U.S. Pat. Nos. 3,868,407, 4,197,254 and 4,199,354.

Close prior art is U.S. Pat. No. 3,923,877, which teaches the reaction of $PhCH_2NHCH_2C(O)OH$ with $H_3PO_3$ and HCHO in dilute HCl at reflux to form $(HO)_2P(O)CH_2N(CH_2OH)CH_2C(O)$ followed by refluxing in aqueous HBr to yield N-phosphonomethylglycine.

Because of the commercial importance of N-phosphonomethylglycine and certain salts as a herbicide, improved methods of preparing these compounds are valuable.

BRIEF DESCRIPTION OF THE INVENTION

This invention relates to a process for preparing N-phosphonomethylglycine which comprises:

(1) reacting a primary amine, $R-NH_2$, with glycolonitrile to form a secondary amine having the structural formula $R-NHCH_2CN$ (2) reacting the secondary amine with formaldehyde and a phosphite having the structural formula $$R^5O-P\begin{matrix}OR^3\\OR^4\end{matrix}$$

to form a tertiary amine having the structural formula $$R-N\begin{matrix}CH_2CN\\CH_2P(O)(OR^3)(OR^4)\end{matrix}$$

and (3) reacting the tertiary amine with hydrohalic acid to form N-phosphonomethylglycine.

DETAILED DESCRIPTION OF THE INVENTION

The process of this invention may be illustrated by the following reaction scheme:

$$R-NH_2 + HOCH_2CN \rightarrow R-NHCH_2CN \quad (a)$$

wherein R is tertiary butyl or $$Ar-\underset{R^2}{\overset{R^1}{\underset{|}{\overset{|}{C}}}}-$$

wherein Ar is an aromatic group, $R^1$ is hydrogen, $C_1-C_{10}$ alkyl or an aromatic group and $R^2$ is hydrogen, $C_1-C_{10}$ alkyl or an aromatic group;

$$R-NHCH_2CN + CH_2O + R^5OP\begin{matrix}OR^3\\OR^4\end{matrix} \longrightarrow \quad (b)$$

$$R-N\begin{matrix}CH_2CN\\CH_2P(O)(OR^3)(OR^4)\end{matrix}$$

wherein R is defined as above and $R^3$ and $R^4$ are both aromatic groups or both aliphatic groups, preferably $R^3$ and $R^4$ are $C_1-C_6$ alkyl, more preferably $C_1-C_4$ alkyl, and $R^5$ is an aliphatic group, preferably $R^5$ is $C_1-C_6$ alkyl, more preferably $C_1-C_4$ alkyl or $R^5$ is hydrogen.

$$R-N\begin{matrix}CH_2CN\\CH_2P(O)(OR^3)(OR^4)\end{matrix} + H_2O \xrightarrow{H^+} HN\begin{matrix}CH_2COOH\\CH_2P(O)(OH)(OH)\end{matrix} \quad (c)$$

wherein R, $R^3$ and $R^4$ are as defined above and H+ is a strong acid such as hydrochloric, hydrobromic, hydriodic, nitric, sulfuric, phosphonic or chloroacetic acid. Preferably H+ is hydrochloric or hydrobromic acid.

The group "$C_1-C_4$ alkyl" encompasses methyl, ethyl, n-propyl, isopropyl, n-butyl, isobutyl, sec-butyl, and tert-butyl. The group "$C_1-C_6$ alkyl" encompasses the same radicals as $C_1-C_4$ alkyl plus the 6 pentyls and the 7 hexyls.

The term "aliphatic group" is used in a broad sense to cover a large class of organic groups characterized by being derived from (1) an acylic (open-chain structure) of the paraffin, olefin and acetylene hydrocarbon series and their derivatives or (2) alicyclic compounds. The aliphatic group can have from 1 to 10 carbon atoms.

The term "aromatic group" is used in a broad sense to distinguish from the aliphatic group and includes a group derived from (1) compounds having 6 to 20 carbon atoms and characterized by the presence of at least one benzene ring, including monocyclic, bicyclic and polycyclic hydrocarbons and their derivatives and (2) heterocyclic compounds having 5 to 19 carbon atoms which are similar in structure and are characterized by having an unsaturated ring structure containing at least one atom other than carbon such as nitrogen, sulfur and oxygen and derivatives of these heterocyclic compounds.

Reaction (a) preferably is run at a temperature between about 0° to about 150° C., more preferably between about 40° C. to about 110° C., and most preferably between about 75° to about 85° C. This reaction step can be run at atmospheric, sub-atmospheric or super-atmospheric pressure, preferably at atmospheric pressure. The reaction is exothermic and proceeds to completion in several hours without external heating. However, external heating can be employed to increase the reaction rate. Normally no solvent is needed for the reaction. Water can be used as a solvent and need not be removed after completion of of the reaction. If a solvent, such as toluene, is used it should be removed after the reaction. Equal mole amounts of the two reactants is preferred.

In reaction (b), preferably equal mole amounts of the secondary amine of reactive step (a), formaldehyde and the phosphite are reacted. The reaction can be carried out by first reacting a mole of the secondary amine with a mole of formaldehyde. This reaction is exothermic and proceeds to completion in one hour. If desired, mole amounts of the secondary amine, formaldehyde and the phosphite can be simultaneously reacted, preferably at a temperature of at least 100° C., most preferably at reflux temperature. Lower temperatures can be used but will result in longer reaction times.

Reaction (c) is carried out by hydrolyzing the tertiary amine of reaction step (b) with 5 moles of water, preferably in the presence of an hydrohalic acid, i.e., hydrochloric acid, hydrobromic acid or hydriodic acid. The first two acids are preferred for economic reasons. Most preferably, the acids are used in concentrated form. For example 37% hydrochloric acid, 46–48% hydrobromic acid and about 55% hydriodic acid are concentrated forms. Less concentrated acids can be used with reduced reaction rates. Preferably, the aqueous solution of the hydrohalic acid can be at least 20% by weight, more preferably 30% by weight. The temperature of the reaction can range from as low as about 90° to about 150° C. or higher, preferably between about 110° C. to about 130° C., most preferably at reflux temperature of the particular hydrohalic acid being employed. At least 3 moles of the acid should be used per mole of tertiary amine. A large excess of acid can be used. Most preferably, 10 to 15 moles of acid are used per mole of tertiary amine. However, higher amounts of up to 100 moles can be used.

The process of this invention can be better understood by reference to the following specific examples.

EXAMPLE I CL N-Benzyl-N-cyanomethyl amine

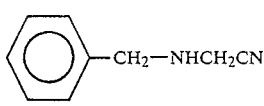

Benzyl amine (10.7 grams, 0.1 mole) was added to 8.2 g (0.1 mole) of a 70% aqueous solution of glycolonitrile, HOCH$_2$CN, in a round-bottom flask. The exothermic reaction mixture was stirred for 3 hours with no external heating. The desired product was not recovered.

EXAMPLE II

O,O-Diethyl-N-benzyl-N-cyanomethyl aminomethylphosphonate

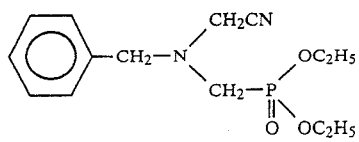

Formaldehyde (37%, 8.2 g, 0.1 mole) was added to the reaction product of Example I and the exothermic reaction mixture was stirred for one hour. Then, 13.8 g (0.1 mole) of diethyl phosphite was added and the mixture was refluxed for 2 hours. On cooling, the reaction mixture wsa combined with 100 milliliters (ml) of diethyl ether and 100 ml of water and phase separated. The organic layer was dried with MgSO$_4$ and evaporated to yield 16 g of the desired product.

The structure was confirmed by infrared (ir), proton nuclear magnetic resonance (nmr) and mass spectroscopy (ms).

EXAMPLE III

N-phosphonomethylglycine

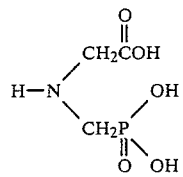

The reaction product of Example II, 13.3 g (0.1 mole) was combined with 50 ml 48% hydrobromic acid and heated to reflux for 3 hours in a 200 ml round-bottom flask equipped with a stirrer and distillation head. The low boiling ethyl bromide was distilled. The reaction product was washed with 50 ml hexane to remove benzyl bromide. Next, the aqueous fraction was stripped under reduced pressure and 50 ml additional 48% hydrobromic acid was added and refluxing was continued for an additional 3 hours. The reaction mixture was cooled, and washed with 50 ml hexane. The aqueous fraction was stripped to yield the desired product, N-phosphonomethylglycine. The product was identified by C$^{13}$ and liquid chromatograph (lc) analysis.

EXAMPLE IV

N-t-Butyl-N-cyanomethyl amine (CH$_3$)$_3$C—NHCH$_2$CN t-Butyl amine (25.7 ml (0.25 mole) was added to 21.0 g (0.26 mole) of a 70% aqueous solution of glycolonitrile, HOCH$_2$CN, in a round-bottom flask. The exothermic reaction mixture was stirred until it cooled and then heated with a steam bath for 15 minutes. The desired reaction product was not recovered.

EXAMPLE V

O,O-Diethyl-N-t-butyl-N-cyanomethyl aminomethylphosphonate

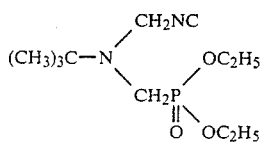

Formaldehyde (37%, 20.0 g, 0.25 mole) was added to the reaction product of Example I and the exothermic reaction mixture was stirred. After 15 minutes, 35.0 g (0.25 mole) of diethyl phosphite was added and the mixture was stirred for 2 hours at room temperature. The mixture was refluxed for 1.5 hours. On cooling, the reaction mixture was combined with 150 milliliters (ml) of diethyl ether and 50 ml of water and phase seperated. The organic layer was dried with MgSO₄ and the solvent stripped to yield 41.0 g of the desired product. The structure was confirmed by ir, nmr and ms.

EXAMPLE VI

N-phosphonomethylglycine

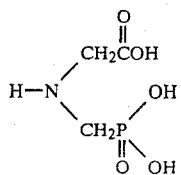

The reaction product of Example V, 5.0 g (0.25 mole) was combined with 25 ml 37% concentrated hydrochloric acid and heated at reflux for 3 hours in a round-bottom flask equipped with a stirrer and reflux condenser. The reaction product was stripped to yield 5.1 g. N-phosphonomethylglycine was identified by lc analysis and proton nmr.

What is claimed is:

1. A compound of the formula

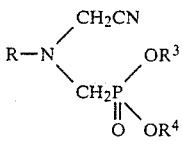

wherein R is tert-butyl or benzyl, $R_3$ is $C_1$–$C_6$ alkyl and $R^2$ is $C_1$–$C_6$ alkyl.

2. The compound of claim 1 wherein $R^3$ is ethyl and $R^4$ is ethyl.

3. The compound of claim 1 wherein R is tert-butyl, $R^3$ is ethyl and $R^4$ is ethyl.

* * * * *